United States Patent [19]
Thomas et al.

[11] Patent Number: 5,131,103
[45] Date of Patent: Jul. 21, 1992

[54] INTEGRATED BACK SUPPORT AND BED APPARATUS AND METHOD

[76] Inventors: Jimmy W. Thomas; Bobbi G. Thomas, both of 810 Brandywine, Temple, Tex. 76504; Charles F. Kallina, III, 3210 Stratford Dr., Temple, Tex. 76502

[21] Appl. No.: 629,433

[22] Filed: Dec. 18, 1990

[51] Int. Cl.⁵ .................... A61C 7/00; A61F 5/04
[52] U.S. Cl. ........................... 5/601; 128/870
[58] Field of Search ..................... 5/60–64, 5/81 R, 82 R; 128/84 C, 87 B, 870, 872, 873; 378/209

[56] References Cited

U.S. PATENT DOCUMENTS

| | | | |
|---|---|---|---|
| 3,434,165 | 3/1969 | Keane | 5/61 |
| 3,584,321 | 6/1971 | Buchanan | 5/62 X |
| 3,783,863 | 1/1974 | Kliever | 5/61 X |
| 3,820,176 | 6/1974 | Feiertag | 5/63 |
| 3,851,644 | 12/1974 | Slagle | 128/870 X |
| 4,244,358 | 1/1981 | Pyers | 5/61 X |
| 4,356,577 | 11/1982 | Taylor et al. | 5/81 R X |
| 4,584,989 | 4/1986 | Stith | 378/209 X |
| 4,890,605 | 1/1990 | Rosendale | 128/84.6 X |
| 4,912,787 | 4/1990 | Bradcovich | 5/62 |
| 4,926,457 | 5/1990 | Poehner et al. | 378/209 |
| 4,953,244 | 9/1990 | Koerber, Sr. et al. | 5/60 |

Primary Examiner—Michael F. Trettel
Attorney, Agent, or Firm—J. Nevin Shaffer, Jr.; Russell D. Culbertson

[57] ABSTRACT

An integrated back support and bed having a removable back support supported by a bottom which is attached to a maneuverable bed and frame. The back support is designed to be taken to the victim of spinal trauma, the victim placed thereon and never removed until treatment is substantially completed. The back support is made of radiolucent material and the bed frame and other parts are made of non-magnetic material so that the back support and bed may be located directly next to magnetic resonance imaging devices, cat scans and the like, without hindering diagnosis. A front support, also removably attachable to the bed and frame, can be sucked into a thin shell by means of common hospital suction lines. The deflated front support is then placed over the user, secured in place, and allowed to reinflate so that it conforms exactly to the dimensions and shape of the user. The user is now held carefully in place and may be rotated from the supine to the prone position without fear of movement and additional injury. In that position the bottom is removed, the back support is removed and access to the user's back for surgery, treatment, diagnosis and the like, is provided. Further, the bed has independently moveable ends which enable high bed tilt angles without raising or lowering the bed and user extreme distances.

16 Claims, 5 Drawing Sheets

INTEGRATED BACK SUPPORT AND BED APPARATUS AND METHOD

BACKGROUND OF THE INVENTION

This invention relates to an improved integrated back support and bed for preventing additional injury to accident victims during transportation to the hospital, examination, initial therapy and surgery at the hospital, and rehabilitation.

A wide variety of devices have been known in the art for quite some time that attempt to maintain spinal stability in spinal trauma patients before, during and after definitive treatment or surgery. For example, patient beds are known that rotate to provide access in examination of the patient and nursing care. Examples of such rotating patient beds are disclosed in Hogan, Stryker, Keane, Vezina, Viamonte, Jr., and Leininger et al., U.S. Pat. Nos. 2,690,177; 3,302,218; 3,434,165; 3,655,178; 3,778,049; and 4,175,550 respectively.

Patient treatment beds are also known in the art that are more or less radiographically transparent such as disclosed in Kok, Franke et al., Williams, Chapa, Hopper et al., Cooper et al., Mirabella, Jelsma et al., Moore et al., and Saussereau, U.S. Pat. Nos. 3,449,570; 3,631,241; 3,631,242; 3,814,414; 3,818,516; 3,947,686; 4,262,204; 4,566,445; 4,718,077; and 4,779,858 respectively.

Although knowledge, diagnostics, and treatment have progressed at an astronomical rate, the means of providing interim spinal stability has not changed significantly in the past forty years. Standard spinal cord injury management, known in the art, requires that the patient be placed on a rigid backboard at the scene of the injury for transportation to the nearest trauma center that has facilities for scanning, treating, managing, and operating on these patients. Due to the current backboard's physical shape and material composition, the patient cannot long remain on the board during the early, and most critical stages of care. Throughout the diagnostic and early treatment phases, the care givers must manually manipulate (i.e. lift, scoot, and turn) the patient between and during each procedure. If the patient has cervical traction via suspended weights, the weights must be removed and an estimated amount of manual traction applied while transporting the patient to and from the intensive care unit (ICU) as well as during the diagnostic procedure.

Drawbacks to the patient beds known in the art are that patients may not comfortably or safely be left on the boards very long without acquiring beds sores, there is no provision in the prior art boards for access to the patient for diagnosis and waste removal, there is no ability for rotating patients safely front to back, and there is no means for providing traction on or off the patient bed. Thus, there is a need in the art for providing an integrated back support and bed which enables diagnosis, particularly radiological, and waste removal, which enables use for extended periods of time on the bed without creating sores, which is maneuverable front to back and which supports the patient front and back, and which incorporates a strain gauge and weightless traction device for providing traction on or off the bed. It, therefore, is an object of this invention to provide an improved integrated back support and bed apparatus for preventing additional injury to accident victims, for providing comfortable support front and back, for allowing movement and diagnosis front and back, for providing weightless traction on or off the bed frame and, for facilitating nursing care and treatment, including surgery.

SHORT STATEMENT OF THE INVENTION

Accordingly, the integrated back support and bed of the present invention includes a removable back support with access means in the back support so that diagnostic tools, x-ray film, and the like, may be inserted therein and so that waste removal is facilitated while the user is supported thereby. A maneuverable bed is provided to which the back support is removably attachable. A matching front support, that is also removably attachable to the back support and the bed, is provided so that when the bed is maneuvered, rotated, inclined, and the like, the user is supported front and back. Finally, a strain gauge and weightless traction device is attached to the back support for providing traction on or off the bed. In the preferred embodiment, the back support itself is constructed of non-magnetic, radiolucent material and is covered with pressure relief material, such as gel or foam, so that the user can remain on the back support for extended periods. The bed is manually and automatically adjsutable into a plurality of position including tilting, front to back, and rotating side to side; prone; supine; trendelenburg and reverse trendelenburg.

BRIEF DESCRIPTION OF THE DRAWINGS

Other objects, advantages, and features of the present invention will become more fully apparent from the following detailed description of the preferred embodiment, the appended claims and the accompanying drawings in which:

DETAILED DESCRIPTION OF THE PREFERRED EMBODIMENT

The preferred embodiment of the present invention is illustrated by way of example in FIGS. 1-10. With specific reference to FIG. 1, integrated back support and bed 10 includes back support 12, bed 14, frame 16 and opposite end supports 18 and 20. Opposite end supports 18 and 20 rise, hydraulically, up and down base columns 21. Frame 16 further includes wheel supports 22 and wheels 24. Automatic rotating device 26 is attached to frame support 28 at one end and to manual rotating devices 30 at both ends.

Figure 1:
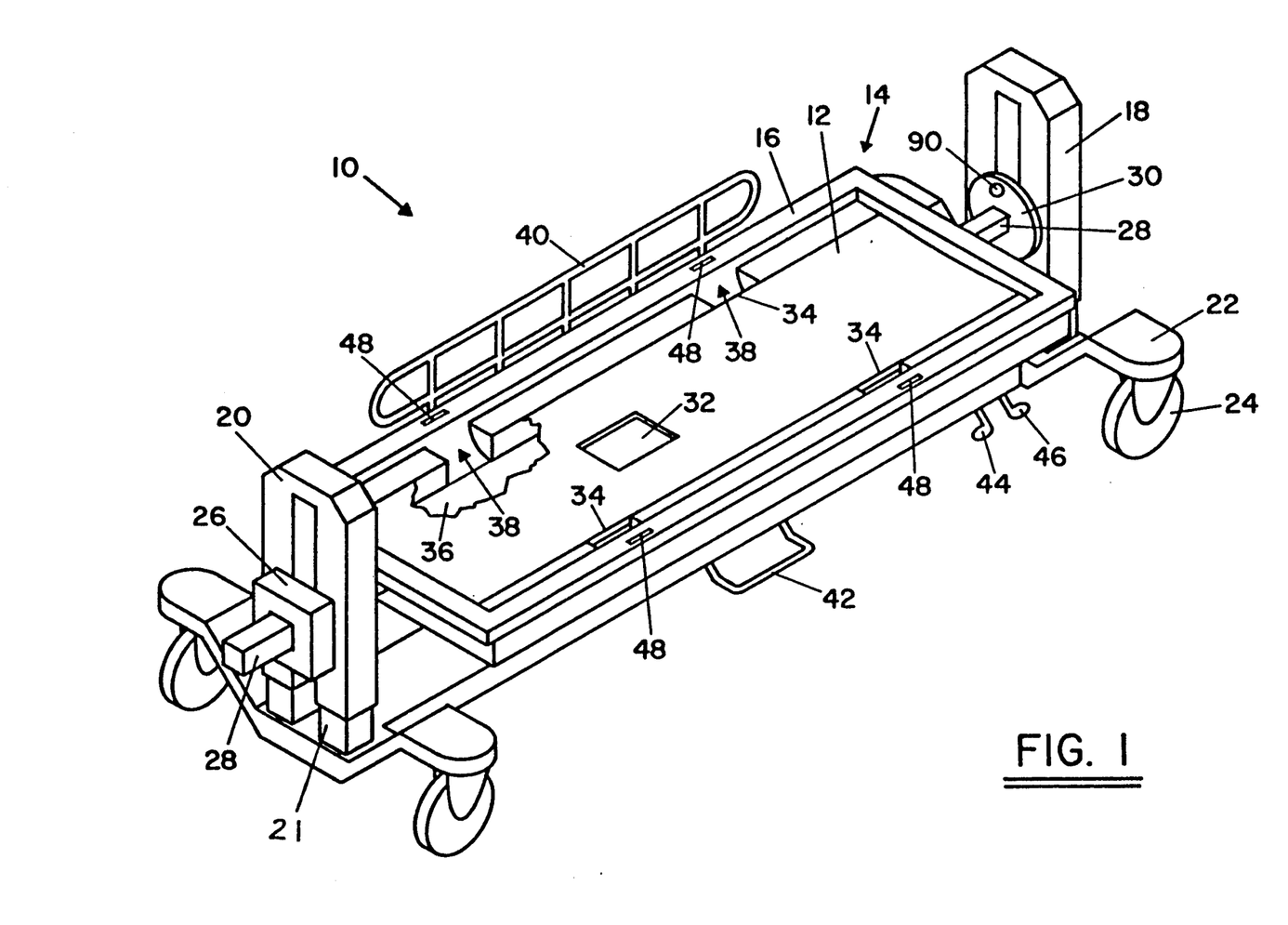
FIG. 1 is a plan vie of a preferred embodiment of the integrated back support and bed of the present invention with the back support partially broken away to reveal the bed frame and bottom support.

Back support 12 has closable waste removal port 32 and a pair of oppositely positioned-handles 34. Bottom 36 supports, back support 12 on frame 16. Frame 16 has hand access slots 38 that just match oppositely-positioned handles 34 so that back support 12 may be easily inserted and removed from bed 14. FIG. 1 also shows one of a pair of guardrails 40 known in the art. The opposite guardrail is removed for clarity. Further, FIG. 1 shows manual foot brake 42 which operates in any known manner to brake wheels 24 and prevent them from moving. Further, mechanical elevation and lowering pedals 44 and 46 are shown for use when the electronic elevation and lowering device, described further hereafter, for tilting the patient front to back and back to front, is inoperative. Further, securing strap holes 48 are shown that are utilized in combination with a strap, not shown, to secure the patient to the back support and bed and, also, to secure the front support to the patient and bed.

Figure 2:
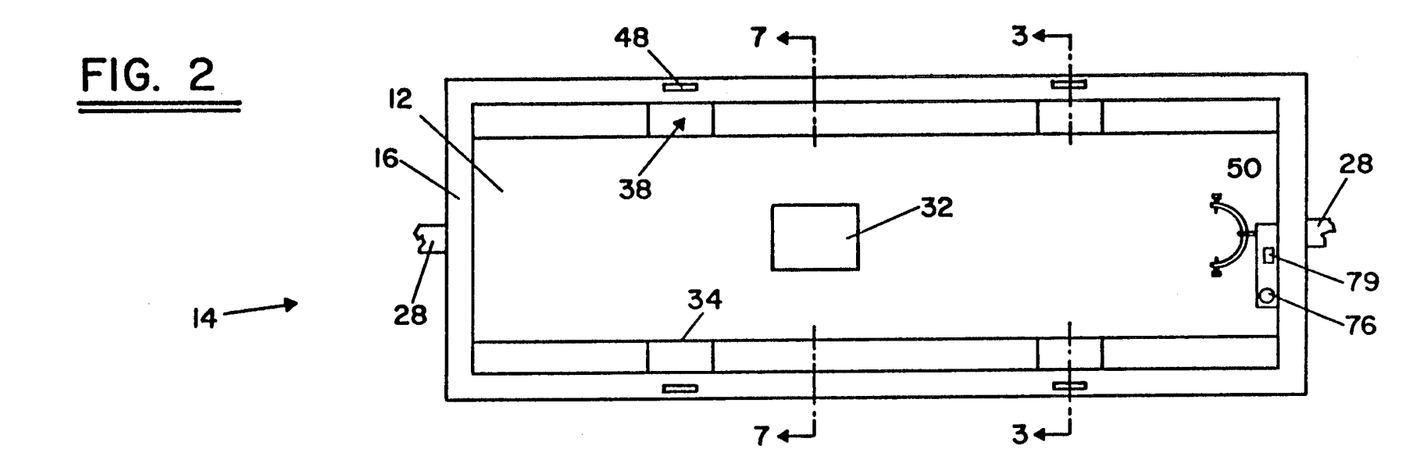
FIG. 2 is a top view of the frame, back support, and strain gauge and weightless traction device.

Referring now to FIG. 2, a top view of the frame of bed 14 is shown without opposite end supports 18 and 20. Strain gauge and weightless traction device 50 is shown attached to back support 12 for providing traction on or off bed 14.

Figure 3:
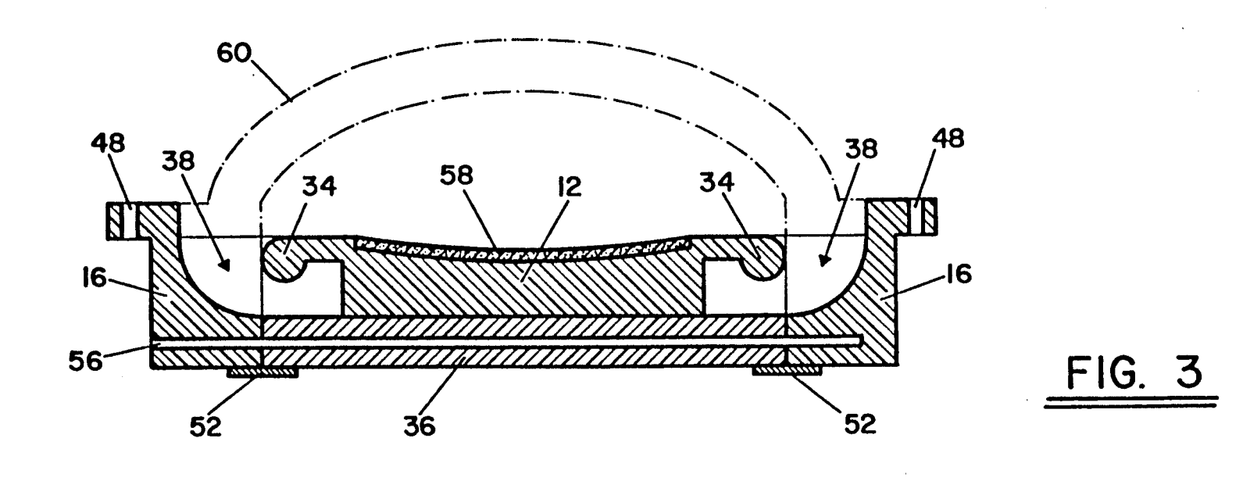
FIG. 3 is a section view taken along the lines 3—3 of FIG. 2 with dotted lines showing the front support in place on the device.

FIG. 3, a section view taken along lines 3—3 of FIG. 2, shows back support 12, with oppositely positioned handles 34 located within hand access slots 38, resting on removable bottom 36. Bottom 36 is held in place by movable supports 52 which are attached to frame 16 by bolts or the like, not shown. Frame 16 includes securing strap holes 48 and diagnostic access slot 56, for x-ray films, medical. .tools and supplies, and the like. Diagnostic slot 56 runs through frame 16 and bottom 36 so that x-ray film, and the like, may be brought in close proximity to a patient/user while on the back support 12. Back support 12 also includes pressure relief foam, gel, and the like 58, known in the art, that enables a patient to remain on back support 12 for extended periods. Shown in dashed lines is front support 60 discussed in detail hereafter.

Figure 4:
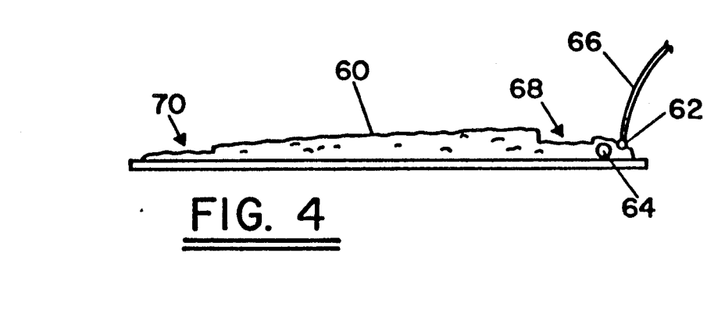
FIG. 4 is a side view of the front support deflated by means of suction.
Figure 5:
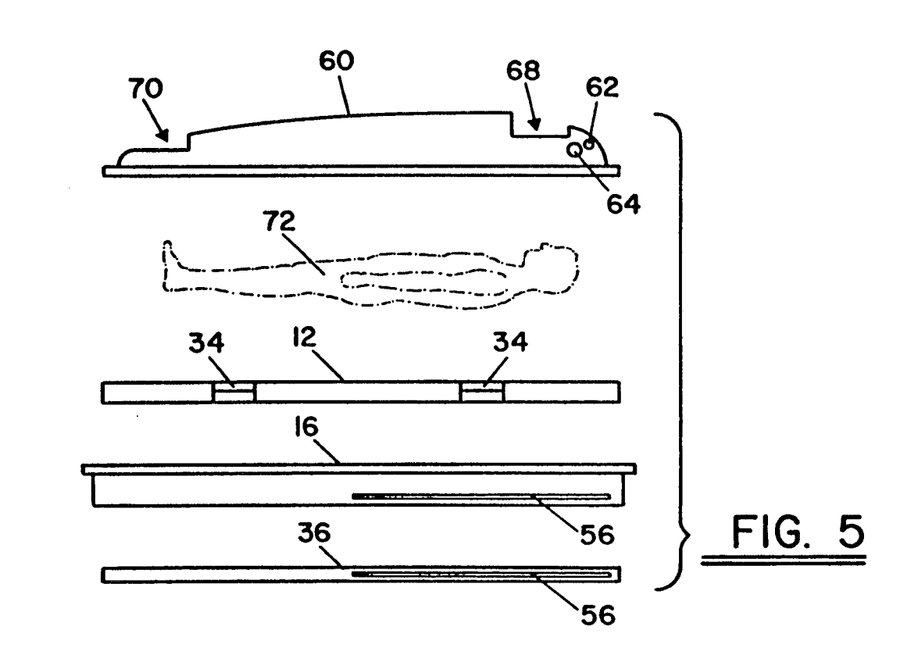
FIG. 5 is an exploded side view showing inflated front support, outline of a patient or user in the supine position, bottom support, frame, and back support.

Referring now to FIGS. 4 and 5, front support 60 is shown in a deflated embodiment in FIG. 4. Front support 60 is comprised of any tough, durable, yet porous and flexible foam, known in the art such as polyurethane foam, capable of supporting several times the weight of a human being in the prone position. Front support 60 is provided with suction valve 62 and suction gauge 64. Suction line 66 is attached to any vacuum line commonly available in a hospital and air is removed from front support 60 so that it is collapsed into a thin shell. Valve 62 is closed, suction line 66 is removed and front support 60 will remain in the thin, compressed state until valve 62 is open.

Referring now to FIG. 5, an exploded view clearly shows face and foot cutouts 68 and 70, respectively, in inflated front support 60. An outline of victim/user 72 in the supine position is shown as well as back support 12, frame 16, and bottom 36.

Figure 6:
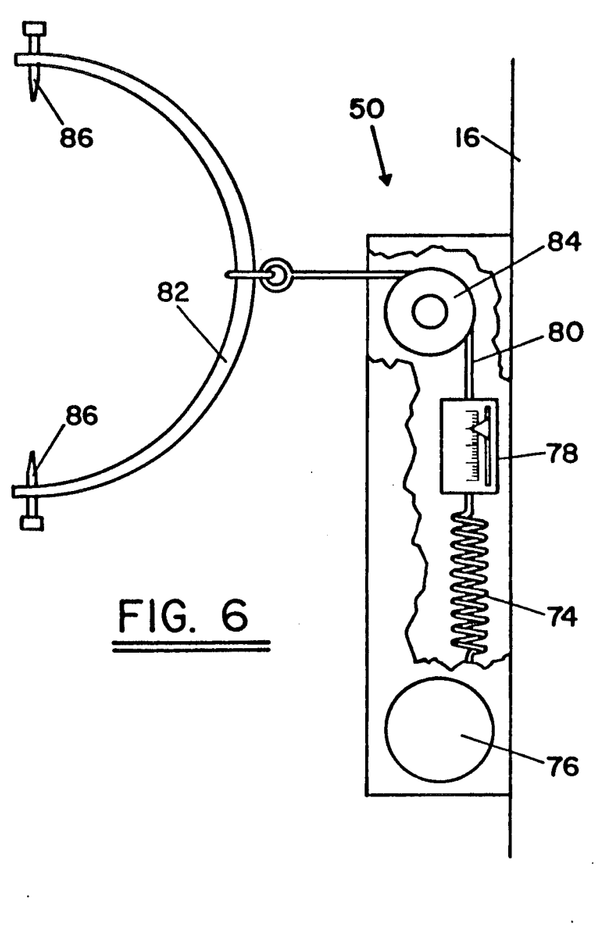
FIG. 6 is a top view of the strain gauge and weightless traction device with the housing being partially broken away to reveal the internal workings of the traction device.

FIG. 6 is a top view of strain gauge and weightless traction device 50 comprised of spring 74 attached at one end to manual tensioner handle 76 and to strain gauge 78 at the other end. Connecting line 80 is attached at one end to strain gauge 78 and at the other to head clamp 82. Connecting line 80 passes around pulley 84 so that tension on user 72's head is parallel to his body. Head clamp 82 has a pair of oppositely positioned head screws 86 designed and known in the art for attachment to trauma victim 72. Strain gauge and weightless traction device 50 is designed to be removably attached to back support 12 and is constructed of non-magnetic material so that once attached to user 72 it need not be removed, as is commonly done now, while the user is being x-rayed or submitted to other diagnostic methods such as magnetic resonance imaging (MRI) cat scans, and the like.

Figure 7:
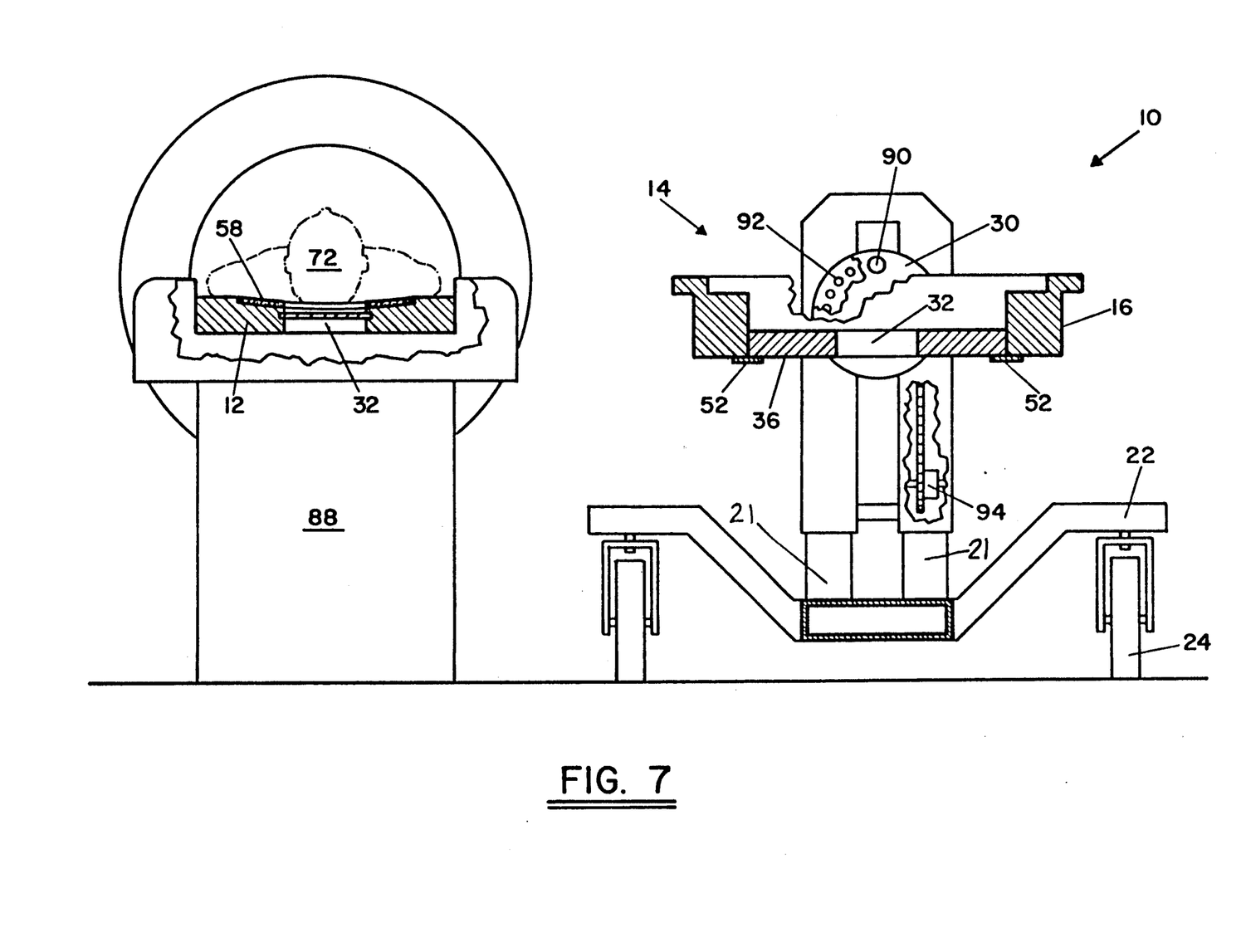
FIG. 7 is a section view taken along the lines 7—7 of FIG. 2 showing the diagnostic and waste removal slots and further showing the user on the back support in a MRI device.

Referring now to FIG. 7, an end view of the device shows the intended use of back support 12 in conjunction with a MRI machine wherein back support 12 is simply lifted in toto from frame 16 and placed onto the rails of the MRI 88. Because back support 12 is composed of non-magnetic, radiolucent material, this and other diagnostic devices can be used to examine the patient without moving victim 72 from back support 12 once the victim is first placed on the back support. As FIG. 7 also illustrates, bed 14 is located directly adjacent to MRI 88, or any other diagnostic device, because it too is made of non-magnetic and radiolucent material such as aluminum, titanium, composite plastics, and the like, so that it may be rolled directly next to the diagnostic device. Further, the end view of bed 14 shows manual rotating device 30 partially broken away. Manual rotating device 30, one at each end of frame 16 and connected to frame support 28, uses spring-loaded ball handle 90 that, when pulled out, enables the user to manually rotate frame 16 to the next of a plurality of detent holes 92 where the ball handle is released and a pin, just matching detent hole 92, enters detent 92 and maintains the bed in the chosen rotated position.

Further referring to FIG. 7, a partial cut away reveals the housing containing the tilting mechanism 94 attached to frame support 28 and located in opposite end supports 18 and 20. As more clearly shown in FIG. 10, the combination enables frame support 28 to move downward in end support 20, on base column 21, and upward at the same time in end support 18, on its base column 21, thereby effectively increasing the angle of tilt front to back and/or back to front while keeping bed 14 at manageable height levels. That is, prior art devices attempting to obtain degrees of tilt provided by Applicant's bed have been unable to do so without greatly raising one end or the other of the bed. The mechanical operation of tilting mechanism 94 performs in the manner of a fork lift device and other devices known in the art and is not described in detail. In general, however, a hydraulic cylinder, not shown, causes opposite ends 18 and 20 to move up or down the length of base column 21. By a combination of sprockets and gears arranged in a two to one ratio, a movement of opposite ends 18 or 20 one foot up or down base column 21 results in a two foot movement of bed 14 thus positioning bed 14 three feet from its starting position.

Figures 8, 9, 10:
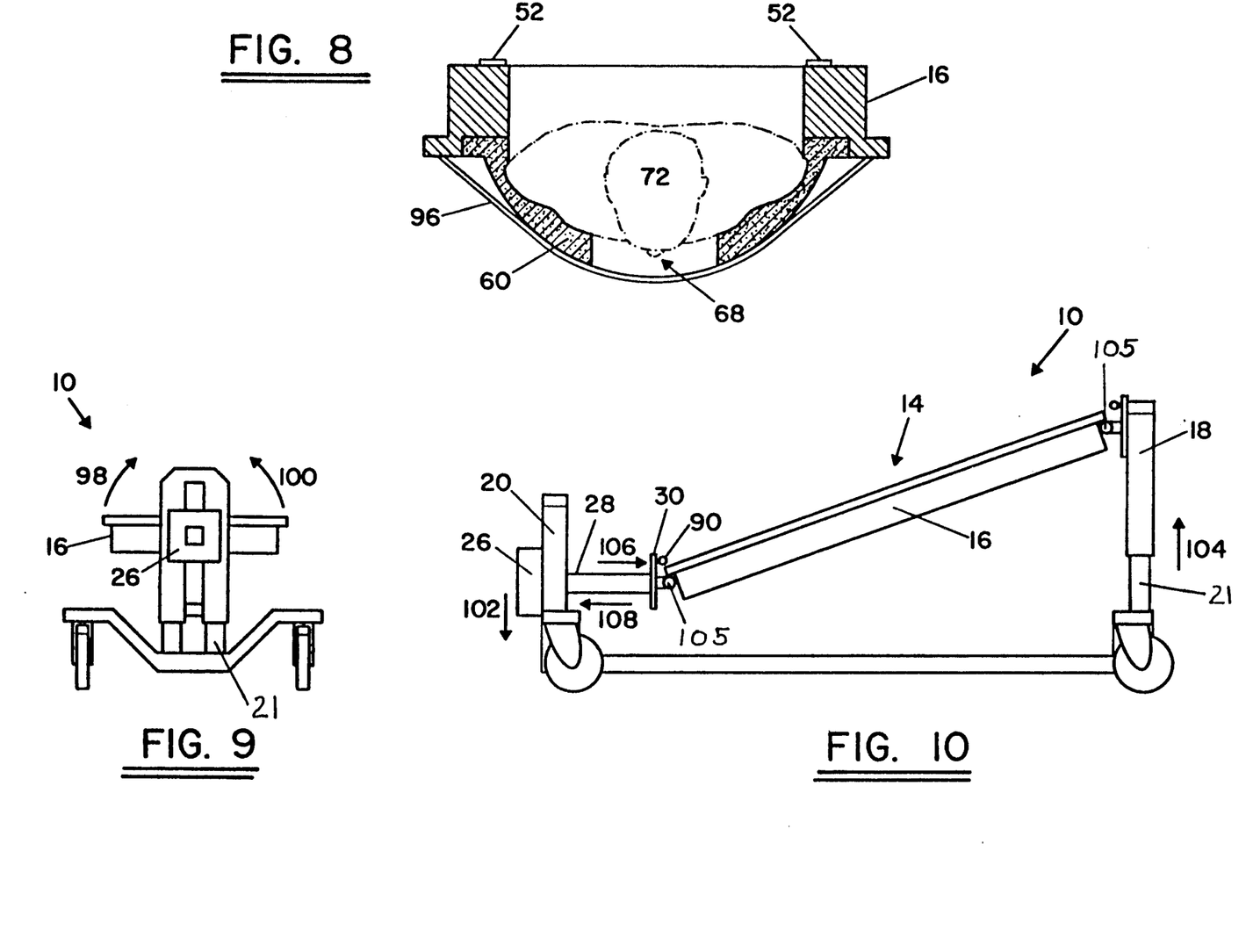
FIG. 8 shows a user in the fully inflated front support device rotated to the prone position for surgery, examination, etc.
FIG. 9 is an end view of the maneuverable bed with arrows indicating the rotational ability of the device.
FIG. 10 is side view of the maneuverable bed indicating the bed's ability to tilt front to back and back to front.

Referring now to FIG. 8, user 72 is shown in the prone position and one of the major advantages of Applicant's invention is illustrated thereby. Front support 60 is shown conformed substantially identically to the user's body by having placed front support 60 on user 72 in the deflated condition. Once placed on user 72, suction valve 62 is opened and front support 60 is allowed to inflate and conform to the user's body. Front support 60 is held in close proximity to user 72 by means of straps 96 which secure front support 60 to frame 16 by means of securing strap holes 48. Obviously, more straps and holes could be applied as necessary. FIG. 8 also illustrates that moveable bottom supports 52 have been moved out of the way so that once user 72 is rotated into the prone position, the access to the victim's back for surgery, diagnosis, or otherwise is provided as follows. Movable bottom supports 52 are rotated out of contact with bottom 36 and bottom 36 is removed. Then back support 12 is simply removed and thereafter, as shown in FIG. 8, user 72 is supported securely and comfortably within front support 60. Should user 72 be required to be rotated to the supine position, the reverse procedure is followed. That is, back support 12 is placed in contact with user 72, bottom 36 is placed in contact with back support 12, movable bottom supports 52 are rotated into position to hold bottom 36 in place and bed 14 is rotated as desired.

Referring now to FIG. 9 and 10, the rotational and tilting abilities of integrated back support and bed 10 are demonstrated. As shown in FIG. 9, by means of automatic or manual methods frame 16 and back support 12 and/or front support 60 may be rotated in the plurality of clockwise directions shown by arrow 98 or in counterclockwise directions shown by arrow 100. FIG. 10 shows that frame support 28 is longer o the end attached to opposite end support 20. Constructing frame support 28 with this extra length at that end enables integrated back support in bed 10 to achieve high degrees of tilt with relatively small up and down motion. In order to achieve the high degree of tilt illustrated in FIG. 10 for example, lowering the tilting mechanism 94 in opposite end 20 moves frame support 28 in the downward direction of arrow 102. At the same time, tilting mechanism 94 in end support 18 moves frame support 28 in the upward direction of arrow 104. Frame 16 is free to move on hinges 105. As a result, frame support 28 at end 20 moves horizontally in the direction of the right hand arrow 106. When back support and bed 10 are moved to a horizontal position, from this extreme tilted position, frame support 28 moves in the horizontal direction of left hand arrow 108.

In operation then, victim/user 72 is located by emergency personnel. Emergency personnel have with them back support 12. Back support 12 has two pairs of oppositely positioned handles 34 that are easy to grip and provide secure hand holds. Victim 72 is secured to back support 12 by any means known in the art, not shown, such as straps, tape, bedding or the like. Once victim/user 72 is secured to back support 12, strain gauge and weightless traction device 50 can be attached to back support 12, as needed. Because the typical dangling weights are not involved, strain gauge and weightless traction device 50 can be attached to user 72 once, and left in place. The traction device is designed to be made of non-magnetic material so that it may be left on the victim as long as necessary throughout diagnostic procedures, examination, treatment and therapy.

Once the victim/user 72 reaches the emergency trauma treatment center, back support 12 is integrated with bed 14. Initially bed 14 has an empty frame 16. Frame 16 has movable bottom supports 52 that are rotated into position and then bottom 36 is placed securely on them. When this is done back support 12 can be placed directly on top of bottom 36. Frame 16 has hand access slots that just match oppositely positioned handles 34 in back support 12. As a result, if necessary, back support 12 can easily be removed from frame 16. Back support 12 and bottom 36 have matching closeable waste removal ports 32. As a result, user 72 can be left on back support 12 much longer than is now the case and in much more sanitary conditions since waste removal is facilitated. Once back support 12 is located in frame 16, back support 12 can be securely attached to frame 16 by means of straps 96 that attach to frame 16 by means of securing strap holes 48. Once victim/user 72 is securely attached to frame 16 it may be rotated clockwise or counterclockwise manually or automatically as desired. Automatic rotating device 26, an electrically/mechanically operated device, such as are known in the art and not disclosed further herein, can be used to rotate user 72 in clockwise direction 98 or counterclockwise direction 100 as desired. Rotation of user 72 is often desired in order to prevent bed sores, provide for better diagnostic views, etc. Manual rotating devices 30 are provided if electricity is not available. Diagnostic access slots in frame 16 and bottom 36 enable the use of diagnostic devices such as x-ray film and the like to be brought in close proximity to use 72 without having to move user 72 from back support 12.

Front support 60 is designed of rugged, collapsible material capable of supporting several times the weight of an ordinary person in the prone position. By connecting suction line 66 to any vacuum line commonly found in emergency rooms, and elsewhere, in hospitals, air can be removed from front support 60. Suction valve 62 can be closed when appropriate suction, as indicated by suction gauge 64, has been reached. In the collapsed state, front support 60 forms a thin shell. When preparing to rotate the user 72 from his back to his front, the user 72 is placed on his back on back support 12 as previously described. Once front support 60 has been deflated it is carefully placed over user 72 and secured in position by straps 96. At that time, suction valve 62 is open, air is reintroduced to front support 60 and front support 60 molds itself to the exact contours of user 72. At this point, user 72 may be rotated securely, without fear of movement or further injury, to the prone position. Once in the prone position bottom 36 is removed, back support 12 is removed and user 72 may be operated upon, x-rayed, and examined in any manner for an extended period of time.

The double acting movement of end supports 18 and 20 in combination with elongated frame support 28 at end 20 enables integrated back support and bed 10 to achieve high tilt angles without substantially raising and lowering the user 72 above the ground. That is, prior art devices could only raise or lower one end. By means of the double acting opposite end supports 18 and 20 on base columns 21 of the present invention high degrees of tilt angles may be achieved while maintaining the user relatively close to the ground. This is because when one end rises the other end is free to drop. In order to accommodate the lengthening angle as the tilt increases, frame support 28 is elongated on end 20 and is allowed to move left and right in directions of arrows 106 and 108 as occurring.

FIG. 7 demonstrates another major advantage of integrated back support and bed 10 by showing bed 14 located in close proximity to magnetic resonance imaging device (MRI) 88. This is possible because bed 14 is made of non-magnetic materials which do not interact with MRI 88 or other diagnostic devices in any appreciable way. Further, the advantages of the back support 5 and bed 10 of the present invention are illustrated in FIG. 7 by showing that user 72 has been removed from bed 14 while still located on the same back support 12 on which he was placed when the first emergency personnel reached him. The back support 12 is designed to just fit within diagnostic devices known in the art and is made of radiolucent material so that the transfer of victim 72 from bed 14 to diagnostic device 88 and back again, as presently occurs, is eliminated and the user remains fully supported by, and is moved only once onto, the back support 12. Victim 72 can remain for extended periods of time on back support 12 because of pressure relief gel 58.

Further, a temperature regulating device, in a preferred embodiment, is attached to the bed so that the temperature of the bed, and the patient can be regulated. Also, weight sensing and measuring devices, in a preferred embodiment, are attached to the bed so that the weight of the patient can be monitored constantly. Such temperature and weigh measuring devices to be used are available and known in the art and not disclosed further herein.

While the integrated back support and bed of the present invention has been disclosed in connection with spinal trauma victims, it should be appreciated that the device can be used in other hospital arenas. The present invention provides an improved back support and bed that can be easily manipulated in order, for example, to rotate, elevate and lower the user. These advantages lend utility to the invention in any hospital situation where extended bed care is indicated. Thus, the integrated back support and bed of the present invention has the important advantage of providing a safe, secure and maneuverable means of handling patients no matter what their injury.

While the present invention has been disclosed in connection with the preferred embodiment thereof, it should be understood that there may be other embodiments which fall within the spirit and scope of the invention as defined by the following claims.

What is claimed is:

1. An integrate back support and bed apparatus comprising:
   a) a removably attachable back support means;
   b) access means in said back support means so that diagnostic means may be inserted therein and so that waste removal is facilitated while a user is supported thereby;
   c) a maneuverable bed means to which said back support means is removably attached;
   d) a matching front support means removably attachable to said back support means and said bed means so that when said bed means is maneuvered the user is supported front and back;
   e) a strain gauge and weightless traction means attached to said back support means for providing traction on or off said bed means;
   f) said back support means of non-magnetic, radiolucent material;
   g) pressure relief means attached to said back support means so that said user can remain on said back support means for extended periods;
   h) diagnostic film slots so that diagnostic films may be taken without removing said user from said back support means;
   i) compartments in said back support means for holding medicines, tools and medical accessories;
   j) automatic rotation means for automatic rotation of said user prior to cervical stabilization;
   k) said bed means maneuverable into a plurality of positions including tilting, front to back and back to front; prone; supine; trendelenburg and reverse trendelenburg;
   l) attachment means for removably attaching said front support means to said back support means and to said bed means so that said plurality of positions, such as the prone position, are permitted;
   m) a face portion means open to provide access and allow communication by said user; and
   n) pressure relief means attached to said front support means so that said user can remain on said front support means for extended periods.

2. The apparatus of claim 1 wherein said strain gauge and weightless traction means further comprises:
   a) an imaging compatible strain gauge attached to said back support means; and
   b) a weightless imaging compatible traction means attached to said back support means so that once attached to said user and once said user is located on said back support means, neither need be removed during image processing, surgery, stabilization in ICU, and thereafter.

3. The apparatus of claim 2 further comprising:
   a) temperature regulating means attached to said bed means so that the temperature of said bed means and said user can be regulated; and
   b) weight sensing and measuring means attached to said bed means so that the weight of said user can be monitored.

4. A spinal trauma support system comprising:
   a) a removably attachable back support means;
   b) access means in said back support means so that diagnostic means may be inserted therein and so that waste removal is facilitated while a user is supported thereby;
   c) a maneuverable bed means to which said back support means is removably attached;
   d) a matching front support means removably attachable to said back support means and said bed means so that when said bed means is maneuvered the user is supported front and back;
   e) a strain gauge and weightless traction means attached to said back support means for providing traction on or off said bed means;
   f) said back support means comprised of non-magnetic, radiolucent material;
   g) pressure relief means attached to said back support means so that said user can remain on said back support means for extended periods in comfort and without suffering bedsores;
   h) automatic rotation means attached to said bed means for automatic rotation of said user prior to cervical stabilization;
   i) said bed means maneuverable into a plurality of positions including tilting, front to back and back to front; prone; supine; trendelenburg and reverse trendelenburg;
   j) attachment means for removably attaching said front support means to said back support means and to said bed means so that said plurality of positions, such as the prone position, are permitted;

k) a face portion means in said front support means open to provide access and allow communication by said user; and l) pressure relief means attached to said front support means so that said user can remain on said front support means for extended periods in comfort and without bedsores.

5. The apparatus of claim 4 wherein said access means further comprises:
a) diagnostic film slots so that diagnostic films may be taken without removing said user from said back support means; and
b) compartments for holding medicines, tools and medical accessories.

6. The apparatus of claim 5 wherein said strain gauge and weightless traction means further comprises:
a) an image compatible strain gauge attached to said back support means; and
b) a weightless imaging compatible traction means attached to said back support means so that once attached to said user and once said user is located on said back support means, neither need be removed during imaging processing, surgery, stabilization in ICU, and thereafter.

7. The apparatus of claim 6 further comprising:
a) temperature regulating means attached to said bed means so that the temperature of said bed means and said user can be regulated; and
b) weight sensing and measuring means attached to said bed means so that the weight of said user can be monitored.

8. A spinal trauma support method comprising the steps of:
a) constructing a removably attachable back support means;
b) providing access means in said back support means so that diagnostic means may be inserted therein and so that waste removal is facilitated while a user is supported thereby;
c) providing a maneuverable bed means to which said back support means is removably attached;
d) removably attaching a matching front support means to said back support means and said bed means so that when said bed means is maneuvered said user is supported front and back;
e) attaching a strain gauge and weightless traction means to said back support means for providing traction on or off said bed means;
f) constructing said back support means of non-magnetic, radiolucent material;
g) attaching pressure relief means to said back support means so that said user can remain on said back support means for extended periods;
h) constructing diagnostic film slots in said back support means so that diagnostic films may be taken without removing said user from said back support means;
i) constructing compartments for holding medicines, tools and medical accessories in said back support means and bed means;
j) attaching automatic rotation means to said bed means for automatic rotation of said user prior to cervical stabilization;
k) maneuvering said bed means into a plurality of positions including tilting, front to back and back to front; prone; supine; trendelenburg and reverse trendelenburg;
l) adding attachment means for removably attaching said front support means to said back support means and to said bed means so that said plurality of positions, such a the prone position, are permitted;
m) constructing a face portion means in said front support means open to provide access and allow communication by said user; and
n) attaching pressure relief means to said front support means so that said user can remain on said front support means for extended periods.

9. The method of claim 8 further comprising the steps of:
a) attaching an imaging compatible strain gauge to said back support means; and
b) attaching a weightless imaging compatible traction means to said back support means so that once attached to said user and once said user is located on said back support means, neither need be removed during image processing, surgery, stabilization in ICU, and thereafter.

10. The method of claim 9 further comprising the steps of:
a) attaching a temperature regulating means to said bed means so that the temperature of said bed means and said user can be regulated; and
b) attaching weight sensing and measuring means to said bed means so that the weight of said user can be monitored.

11. A spinal trauma support method comprising the steps of:
a) constructing a removably attachable back support means;
b) providing access means in said back support means so that diagnostic means may be inserted therein and so that waste removal is facilitated while said user is supported thereby;
c) providing a maneuverable bed means to which said back support means is removably attached;
d) removably attaching a matching front support means to said back support means so that when said bed means is maneuvered, the user is supported front and back;
e) attaching a strain gauge and weightless traction means to said back support means for providing traction on or off said bed means;
f) constructing said back support means of non-magnetic radiolucent material;
g) attaching pressure relief means to said back support means so that said user can remain on said back support means for extended periods in comfort and without suffering bedsores;
h) attaching automatic rotation means to said bed means for automatic rotation of said user prior to cervical stabilization;
i) maneuvering said bed means into a plurality of positions including tilting, front to back and back to front, prone, supine, trendelenburg and reverse trendelenburg;
j) adding attachment means for removably attaching said front support means to said back support means and to said bed means so that said plurality of positions, such as the prone position, are permitted;

k) constructing a face portion means in said front support means open to provide access and allow communication by said user; and l) attaching pressure relief means to said front support means so that said user can remain on said front support means for extended periods in comfort and without bedsores.

12. The method of claim 11 further comprising the steps of:

a) constructing diagnostic film slots in said back support means so that diagnostic films may be taken without removing said user from said back support means; and b) constructing compartments for holding medicines, tools and medical accessories in said back support means and said bed means.

13. The method of claim 12 further comprising the steps of:

a) attaching an imaging compatible strain gauge to said back support means; and b) attaching a weightless imaging compatible traction means to said back support means so that once attached to said user and once said user is located on said back support means, neither need be removed during image processing, surgery, stabilization in ICU, and thereafter.

14. The method of claim 13 further comprising the steps of:

a) attaching temperature regulating means to said bed means so that the temperature of said bed means and said user can be regulated; and b) attaching weight sensing and measuring means to said bed means so that the weight of said user can be monitored.

15. An integrated back support and bed apparatus comprising:

a. a removably attachable back support means;

b. access means in said back support means so that diagnostic means may be inserted therein and so that waste removal is facilitated while a user is supported thereby;

c. a maneuverable bed means to which said back support means is removably attached;

d. a matching front support means removably attachable to said back support means and said bed means so that when said bed means is maneuvered the user is supported front and back, said front support further comprising an expanded soft form collapsible by air suction means prior to placement over said user that, when air is allowed in, expands and conforms to the user; and e. a strain gauge and weightless traction means attached to said back support means for providing traction on or off said bed means.

16. A spinal trauma support method comprising the steps of:

a. constructing a removably attachable back support means;

b. providing access means in said back support means so that diagnostic means may be inserted therein and so that waste removal was facilitated while a user is supported thereby;

c. providing a maneuverable bed means to which said back support means is removably attached;

d. removably attaching a matching front support means to said back support means and said bed means so that when said bed means is maneuvered said user is supported front and back, the step of attaching said front support further comprising the step of collapsing an expanded soft form by air suction means prior to placement over said user that, when air is allowed in, expands and conforms to the user; and e. attaching a strain gauge and weightless traction means to said back support means for providing traction on or off said bed means.

* * * * *